(12) United States Patent
Paik et al.

(10) Patent No.: US 11,298,307 B2
(45) Date of Patent: Apr. 12, 2022

(54) TRANSPARENT OR SEMITRANSPARENT COSMETIC COMPOSITION HAVING ENHANCED AMENTOFLAVONE STABILITY

(71) Applicant: Amorepacific Corporation, Seoul (KR)

(72) Inventors: Byung Ryol Paik, Yongin-si (KR); Soon Ae An, Yongin-si (KR); Joon Young Hwang, Yongin-si (KR); Yong Jin Kim, Yongin-si (KR); Byung Fhy Suh, Yongin-si (KR)

(73) Assignee: Amorepacific Corporation, Seoul (KR)

(*) Notice: Subject to any disclaimer, the term of this patent is extended or adjusted under 35 U.S.C. 154(b) by 143 days.

(21) Appl. No.: 16/499,367

(22) PCT Filed: Mar. 26, 2018

(86) PCT No.: PCT/KR2018/003515
§ 371 (c)(1),
(2) Date: Sep. 30, 2019

(87) PCT Pub. No.: WO2018/182252
PCT Pub. Date: Oct. 4, 2018

(65) Prior Publication Data
US 2020/0054540 A1    Feb. 20, 2020

(30) Foreign Application Priority Data

Mar. 31, 2017    (KR) .................. 10-2017-0041567

(51) Int. Cl.
| A61K 8/49 | (2006.01) |
| A61K 8/34 | (2006.01) |
| A61K 8/67 | (2006.01) |
| A61K 8/97 | (2017.01) |
| A61Q 19/08 | (2006.01) |

(52) U.S. Cl.
CPC .............. *A61K 8/498* (2013.01); *A61K 8/345* (2013.01); *A61K 8/675* (2013.01); *A61K 8/97* (2013.01); *A61Q 19/08* (2013.01); *A61K 2800/262* (2013.01)

(58) Field of Classification Search
None
See application file for complete search history.

(56) References Cited

U.S. PATENT DOCUMENTS

| 2012/0022151 A1* | 1/2012 | Park ..................... A61K 31/352 514/456 |
| 2012/0219604 A1 | 8/2012 | Kim et al. |
| 2014/0031314 A1* | 1/2014 | Morganti ............... A61K 8/735 514/54 |
| 2014/0107046 A1 | 4/2014 | Pan et al. |
| 2015/0005247 A1* | 1/2015 | Chen ..................... A61K 8/891 514/27 |

FOREIGN PATENT DOCUMENTS

| CN | 1562994 A | 1/2005 |
| CN | 105407720 A | 3/2016 |
| JP | 2013-509481 | 3/2013 |
| JP | 2015-533169 | 11/2015 |
| KR | 100669362 B1 * | 1/2007 |
| KR | 10-0781604 B1 | 12/2007 |
| KR | 10-2011-0065055 A | 6/2011 |
| KR | 10-2013-0119587 A | 11/2013 |
| KR | 10-2015-0091468 A | 8/2015 |
| KR | 10-2015-0092102 A | 8/2015 |
| WO | WO-9727841 A1 * | 8/1997 ............... A61K 9/08 |

OTHER PUBLICATIONS

International Search Report for PCT/KR2018/003515 dated Jul. 27, 2018 [PCT/ISA/210].
Japan Patent Office, Communication dated Nov. 9, 2021 in Japanese Application No. 2019-516999 with English Translation.

* cited by examiner

*Primary Examiner* — Gina C Justice
(74) *Attorney, Agent, or Firm* — Sughrue Mion, PLLC

(57) ABSTRACT

The present invention relates to a transparent or semitransparent cosmetic composition in which the stability of amentoflavone is enhanced, and more particularly, to a transparent or semitransparent cosmetic composition, wherein a water-soluble amentoflavone-oligomer complex, in which amentoflavone is encapsulated in a hollow structure of an oligomer structure, is stabilized in a second agent containing a polyhydric alcohol, a two-liquid-type container is used to mix first and second agents before use, and hydrotrope is contained in the first agent to increase the mixing stability of the first and second agents and thereby enhance the stability of amentoflavone.

12 Claims, 1 Drawing Sheet

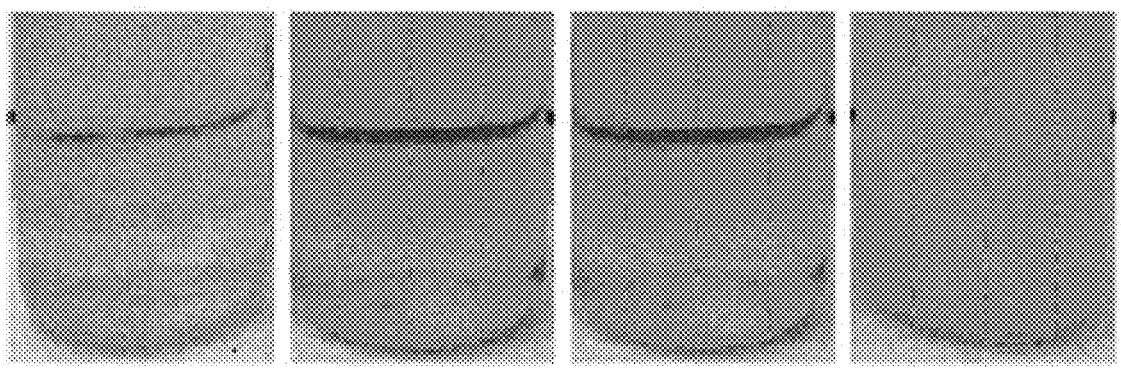

TRANSPARENT OR SEMITRANSPARENT COSMETIC COMPOSITION HAVING ENHANCED AMENTOFLAVONE STABILITY

CROSS REFERENCE TO RELATED APPLICATIONS

This application is a National Stage of International Application No. PCT/KR2018/003515 filed Mar. 26, 2018, claiming priority based on Korean Patent Application No. 10-2017-0041567 filed Mar. 31, 2017, and the disclosure of which is incorporated herein in its entirety.

TECHNICAL FIELD

The present invention relates to a transparent or semitransparent cosmetic composition having enhanced amentoflavone stability, and more particularly to a transparent or semitransparent cosmetic composition having enhanced amentoflavone stability comprising a second agent containing amentoflavone and a polyhydric alcohol, and a first agent containing hydrotrope.

BACKGROUND ART

Amentoflavone is a rare Bi-flavonoid that improves endogenous and exogenous aging at the same time and is a raw material that is effective for skin cell regeneration, damage prevention, wrinkle improvement, and skin moisturization. When amentoflavone is contained in the cosmetic composition at a certain concentration or higher, it corresponds to a functional raw material that can exhibit wrinkle improvement functionality.

However, amentoflavone is a poorly soluble component and has a problem that it is difficult to stabilize in cosmetic compositions for a long period of time. In order to solve this problem, a raw material in which amentoflavone was encapsulated in a cavity structure of an oligomer structure derived from a hydrophilic natural polymer has been developed. As a result, it is possible to dissolve amentoflavone in the aqueous phase, and thus amentoflavone may be used for formulations with low transparency and high viscosity like cream, or amentoflavone may be used by adding in a small amount to a formulation having transparency or low viscosity.

However, even amentoflavone raw materials capable of being dissolved in the aqueous phase in this way cause precipitation in long-term or high-temperature accelerated stability tests when dissolving in the aqueous phase, and thus they have apparent quality problems and have a lower titer. Therefore, it has almost never been used in a transparent or semitransparent cosmetic composition in such a content that the effect of amentoflavone can be expected.

DETAILED DESCRIPTION OF THE INVENTION

Technical Problem

An object of the present invention is to provide a transparent or semitransparent cosmetic composition wherein a water-soluble amentoflavone-oligomer complex, in which amentoflavone is encapsulated in a cavity structure of an oligomer structure, is stabilized in a second agent containing a polyhydric alcohol, a two-liquid type container is used to mix first and second agents before use, and hydrotrope is contained in the first agent to increase the mixing stability of the first and second agents and thereby enhance the stability of amentoflavone.

Technical Solution

In order to achieve the above object, one embodiment of the present invention provides a transparent or semitransparent cosmetic composition having enhanced amentoflavone stability which is compositionally characterized by comprising a first agent containing hydrotrope, and a second agent containing amentoflavone and a polyhydric alcohol for stabilizing the amentoflavone, wherein the first agent and the second agent are respectively contained in a two-liquid type container and mixed before use.

Advantageous Effects

The transparent or semitransparent cosmetic composition according to the present invention is used by placing a second agent containing amentoflavone and a polyhydric alcohol, and a first agent containing hydrotrope into a two-liquid type container and mixing them before use, and therefore, it can enhance the stability of amentoflavone and prevent or delay the precipitation of amentoflavone.

In addition, the cosmetic composition of the present invention stabilizes amentoflavone so as to be contained in an effective amount, and provides excellent wrinkle improvement and skin moisturizing effects due to the inclusion of amentoflavone.

BRIEF DESCRIPTION OF THE DRAWING

FIG. 1 is a diagram showing the results of the eighth week accelerated stability evaluation test according to Test Example 3.

DETAILED DESCRIPTION OF THE EMBODIMENTS

Hereinafter, the transparent or semitransparent cosmetic composition having enhanced amentoflavone stability according to the present invention will be described in more detail.

Unless otherwise specified, the names of the compounds described herein refer to a compound corresponding to the INCI (International Nomenclature Cosmetic Ingredient) Name listed in the International Cosmetic Ingredient Dictionary (ICID) published by the Cosmetic, Toiletry and Fragrance Association (CTFA) of the United States. If the name does not exist among the INCI name, it refers to a compound in accordance with the IUPAC nomenclature established by the International Union of Pure and Applied Chemistry (IUPAC). Further, if no compound in accordance with the IUPAC nomenclature exists, it refers to a compound corresponding to the name of the compound commonly used in the technical field of the present invention.

Unless defined otherwise, all technical and scientific terms used herein have the same meaning as commonly understood by one of ordinary skill in the art to which the invention pertains. Generally, the nomenclature used herein is those well-known and commonly employed in the art.

Amentoflavone used in the present invention is a compound having the following Chemical Formula 1, and are known as functional raw materials contained in *Selaginella tamariscina* extract

[Chemical Formula 1]

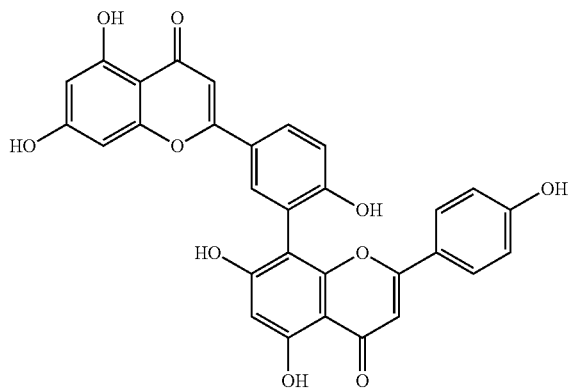

In the cosmetic composition according to the present invention, amentoflavone can be used as a single compound, or it can also be used in the form of *Selaginella tamariscina* extract containing amentoflavone.

*Selaginella tamariscina* is a perennial grass belonging to the Selaginellaceae family, and is largely spread laterally but curled into a fist shape when dried. Thus, the name of herbal medicines is called *Selaginellae herba*.

When amentoflavone is used in the form of *Selaginella tamariscina* extract, the *Selaginella tamariscina* extract is not particularly limited in its production method, and it may be produced by a general method known in the art.

Specifically, the *Selaginella tamariscina* extract can be produced in a powder state by immersing *Selaginella tamariscina* in at least one selected from the group consisting of organic solvents such as ethanol, methanol, butanol, ether, ethyl acetate, chloroform, and a mixed solvent of these organic solvents and water for 4 to 10 days, preferably 7 days, extracting the components and then concentrating them at high temperature, followed by vacuum-drying at 20 to 35° C., preferably 30° C. for 20 to 30 hours, preferably 24 hours.

The transparent or semitransparent cosmetic composition having enhanced amentoflavone stability according to the present invention may comprise a first agent containing hydrotrope, and a second agent containing amentoflavone and a polyhydric alcohol, and it can be made into a transparent or translucent formulation after mixing of the first and second agents.

At this time, the polyhydric alcohol is contained together with amentoflavone in the second agent in order to stabilize the amentoflavone, and it is desirable that the first agent and the second agent are respectively stored in a two-liquid type container and mixed before use.

In addition, the first agent and the second agent may be mixed in a ratio of 1 to 6:1, more preferably in a ratio of 3:1 on a weight basis in order to have the intended effect.

Hereinafter, the components constituting the first agent and the second agent will be described in more detail.

Hydrotropes (or hydrotropic agents) are for enhancing the mixing stability of the first agent and the second agent, and examples thereof may be at least one selected from the group consisting of niacinamide, caffeine, sodium pyrrolidone carbonic acid, sodium salicylate, urea, hydroxyethyl urea, and D-panthenol, but are not limited thereto. More preferably, at least one of niacinamide and D-panthenol may be used.

In addition, the hydrotrope may be included in an amount of 0.1 to 10% by weight, preferably 2 to 7% by weight, based on the total weight of the first agent in order to have the intended effect. If the content of the hydrotrope is less than 0.1% by weight, it cannot fully serve as a hydrotropic agent. If the content of the hydrotrope is more than 10% by weight, it may provide a bad feeling of use and cause irritation to the skin.

Meanwhile, in another embodiment of the present invention, the first agent may contain various cosmetic raw material components in addition to the hydrotrope. Examples of the components useful as the cosmetic raw material components include at least one selected from a solid-phase component including fats, waxes, higher alcohols, higher fatty acids, hydrocarbons and the like, which have a melting point of 30° C. or higher and are solid at room temperature; or a liquid-phase component including oils, esters, ethers, hydrocarbons, and the like.

Specific examples of the solid-phase components include fat such as shea butter, mango seed butter and cacao seed butter, etc.; wax such as myristyl myristate, *Camellia sinensis* leaf extract, jojoba wax, sunflower seed wax, carnauba wax, candelilla wax and beeswax, etc.; higher alcohol such as cetyl alcohol, stearyl alcohol and behenyl alcohol, etc.; higher fatty acid such as caprylic/capric triglyceride, lauric acid, myristic acid, palmitic acid and stearic acid, etc.; hydrocarbon such as ceresin, etc.

Further, examples of the liquid-phase components include oil such as meadowfoam seed oil, sunflower seed oil, macadamia seed oil, green tea seed oil, ginger oil, *ginseng* oil, coconut oil, olive oil and *camellia* oil, etc.; ester such as phytosteryl/octyldodecyl lauroyl glutamate, isostearyl isostearate, methylheptyl isostearate, dicaprylyl carbonate and isopropyl palmitate, etc.; ether such as dicaprylyl ether, etc.; silicone oils such as dimethicone, cyclopentasiloxane, cyclohexasiloxane, phenyltrimethicone, trisiloxane and methyltrimethicone, etc.; and hydrocarbon such as squalane, etc.

In addition, the cosmetic composition according to the present invention may contain an appropriate amount of auxiliary components such as polyol, ethanol, extract, functional efficacy component, coloring agent, flavoring agent, thickening agent, preservative, moisturizing agent, water-soluble efficacy component and the like conventionally used in the manufacture of an oil-in-water cosmetic composition, and preferably, they may be contained in an amount of 0 to 90% by weight based on the total weight of the cosmetic composition.

In one embodiment of the present invention, amentoflavone may be encapsulated in a cavity structure of an oligomeric structure derived from a hydrophilic natural polymer and thus contained in the form of a water-soluble amentoflavone-oligomer complex.

That is, in this specification, the water-soluble amentoflavone-oligomer complex means that the poorly soluble amentoflavone is encapsulated in the cavity structure of the oligomer structure in order to improve the solubility in water.

Specifically, the water-soluble amentoflavone-oligomer complex may be produced by forming a hydrophobic cavity structure with an oligomer structure derived from a natural polymer and encapsulating the amentoflavone in the cavity structure. For example, the water-soluble amentoflavone-oligomer complex may be produced by mixing chitosan and hyaluronic acid, which are oligomer structures derived from natural polymers, to form a hydrophobic cavity structure and encapsulating *Selaginella tamariscina* extract containing amentoflavone into the cavity structure. Moreover, as the oligomer structure having the hydrophobic cavity structure, a commercially available product can be purchased and used.

At this time, the production temperature of the water-soluble amentoflavone-oligomer complex is preferably from 20 to 80° C., and the pH of the solution is preferably maintained at 5 to 8.

On the other hand, the amentoflavone can be encapsulated in the cavity structure in an amount of 7.6 to 9.2% by weight based on the total weight of the water-soluble amentoflavone-oligomer complex in order to have the intended effect. The water-soluble amentoflavone-oligomer complex may be contained in an amount of 0.1 to 5% by weight, preferably 1 to 5% by weight, based on the total weight of the cosmetic composition in order to have the intended effect. That is, the amentoflavone can be contained in an amount of 0.0076 to 0.46% by weight, preferably 0.076 to 0.46% by weight, based on the total weight of the cosmetic composition. If the contents of the amentoflavone and the water-soluble amentoflavone-oligomer complex are less than 7.6% by weight and less than 0.1% by weight, respectively, it is not possible to expect the effect of improving wrinkles and aging. If the contents of the amentoflavone and the water-soluble amentoflavone-oligomer complex exceed 9.2% by weight and 5% by weight, respectively, there is a possibility that the concentration in the formulation is increased and thus the precipitation is accelerated.

Thus, by containing amentoflavone in the form of a water-soluble amentoflavone-oligomer complex, it is possible to increase the solubility of amentoflavone in the aqueous phase. However, even when it is contained in the form of a water-soluble amentoflavone-oligomer complex, the precipitation of amentoflavone occurs, which makes it difficult to make into a transparent or translucent formulation.

Therefore, in one embodiment of the present invention, in order to enhance the stability of the water-soluble amentoflavone-oligomer complex, the polyhydric alcohol may be contained together in the second agent.

As the polyhydric alcohol for enhancing the stability of such amentoflavone, dihydric or trihydric alcohols having 3 to 6 carbon atoms are preferable. Among them, propanediol such as 1,2-propanediol (also known as propylene glycol), 2,2-propanediol, 1,3-propanediol; or butanediol such as 1,2-butanediol, 1,3-butanediol, 1,4-butanediol, 2,3-butanediol are more preferable. However, the present invention is not limited thereto.

Meanwhile, in still another embodiment of the present invention, the second agent may further include a small amount of distilled water or glycerin in addition to the polyhydric alcohol and the water-soluble amentoflavone-oligomer complex. However, the distilled water or glycerin may be contained in an amount of 20% by weight or less, preferably 10% by weight or less, and still more preferably 4% by weight or less, based on the total weight of the second agent in order to have the intended effect. If the content of the distilled water or glycerin exceeds 20% by weight, the stabilization effect of amentoflavone may be reduced and the precipitation may be accelerated.

As such, the reason why it is possible to stabilize when a small amount of distilled water or glycerin is contained in addition to the polyhydric alcohol is that the solubility parameter of the solvent can be adjusted by mixing the solvent, which can improve the solubility of the soluble amentoflavone-oligomer complex.

On the contrary, when ethanol is contained in addition to the polyhydric alcohol, the solubility is decreased, which is not preferable.

At this time, the water-soluble amentoflavone-oligomer complex may be contained in an amount of 0.2 to 30% by weight based on the total weight of the second agent in order to have the intended effect. That is, the amentoflavone may be contained in an amount of 0.0152 to 2.76% by weight based on the total weight of the second agent. If the content of the water-soluble amentoflavone-oligomer complex is less than 0.2% by weight, it is not possible to create a concentration sufficient to expect the efficacy when mixing the first agent and the second agent. If the content of the water-soluble amentoflavone-oligomer complex is more 30% by weight, precipitation is accelerated even in polyhydric alcohol, and stabilization of amentoflavone cannot be expected.

On the other hand, the cosmetic composition according to the present invention may be made into a transparent or translucent formulation such as a softening lotion, an astringent lotion, a nourishing lotion, a cleansing lotion, or an essence. However, the cosmetic composition can be used without limitation as long as it can be formed as a transparent or translucent formulation.

In addition, the cosmetic composition according to the present invention may additionally contain other ingredients that may provide a synergic effect to the main effect, within a range where they do not negatively affect the main effect. Further, the cosmetic composition according to the present invention may further include moisturizing agent, emollient agent, ultraviolet absorbent, antiseptic, fungicide, antioxidant, pH adjuster, flavoring agent, cooling agent, or antiperspirant. The ingredients may be selected by those skilled in the art without difficulty in consideration of the formulation of the cosmetic composition or the purpose of use.

Hereinafter, the present invention will be described in more detail by way of Examples and Experimental Examples. However, these Examples and Experimental Examples are given for a better understanding of the invention only, and the scope of the invention is not intended to be limited by these Examples. Modifications, substitutions, and additions conventionally known in the art are intended to include within the scope of the present invention.

<Reference Example 1> Production of *Selaginella tamariscina* Extract 420 kg of washed *Selaginella tamariscina* was prepared, immersed in ethanol, extracted at room temperature for 7 days, and then filtered through a 250 mesh (3 μm) filter paper. The filtrate was then concentrated at 60° C., which was dissolved in water and extracted three times with ethyl acetate (EtOAc). The ethyl acetate layer was separated and then concentrated at 60° C., and amentoflavone was separated until it was eluted from a silica powder-containing column (eluted with hexane and ethyl acetate=1:1). The separated amentoflavone fraction was concentrated at 60° C., dissolved in ethanol and then filtered through a 0.45 μm filter paper. This was again concentrated at 60° C. and vacuum-dried at 30° C. for 24 hours to produce 1 kg of powdered *Selaginella tamariscina* extract.

<Reference Example 2> Production of Water-Soluble Amentoflavone-Oligomer Complex Chitosan and hyaluronic acid, which are oligomer structures derived from natural polymers, were mixed to form a hydrophobic cavity structure, and *Selaginella tamariscina* extract was encapsulated in the cavity structure, thereby producing a water-soluble amentoflavone-oligomer complex. Specifically, chitosan and hyaluronic acid were mixed at a weight ratio of 6:1 and completely dissolved in water to produce an oligomer structure in which a cavity structure was formed. *Selaginella tamariscina* extract powder was gradually added thereto so that the amentoflavone contained in the *Selaginella tamariscina* extract was encapsulated in the hydrophobic cavity structure of the oligomer structure. Then, the reaction solution was filtered or centrifuged to remove the residual *Selaginella tamariscina* extract that was not encapsulated in the oligomer structure. Water and an organic solvent were removed from the reaction solution from which the residue was removed, followed by drying to produce a water-soluble amentoflavone-oligomer complex. At this time, the production temperature was 40 to 50° C. and the pH was maintained at 6.5 to 7.5.

Here, the content of amentoflavone was 76 to 92% by weight based on the total weight of *Selaginella tamariscina* extract, and *Selaginella tamariscina* extract was contained in an amount of 7.6 to 9.2% by weight based on the total weight of the water-soluble amentoflavone-oligomer complex.

<Production Example 1> Production of Second Agent

The components were mixed in accordance with the composition of Table 1 below and mixed thoroughly for 30 minutes or more in a mixer and completely dissolved to prepare Examples 1 to 4 and Comparative Examples 1 to 7. The unit of content in Table 1 below is the weight percent of the components corresponding to the total weight of the second agent.

weight percent of the components corresponding to the total weight of the first agent.

TABLE 2

| | Component | Content (wt %) | | | |
|---|---|---|---|---|---|
| | | Example 5 | Example 6 | Example 7 | Comparative Example 8 |
| Water-soluble part | D.I. Water | 82.36 | 79.36 | 77.36 | 84.36 |
| | EDTA-2Na | 0.02 | 0.02 | 0.02 | 0.02 |
| | Glycerin | 4.00 | 4.00 | 4.00 | 4.00 |
| | Butylene Glycol | 4.00 | 4.00 | 4.00 | 4.00 |
| | Hydroxyethyl Cellulose | 0.10 | 0.10 | 0.10 | 0.10 |
| | Niacinamide | 2.00 | | 2.00 | |
| | D-panthenol | | 5.00 | 5.00 | |
| | Glyceryl Polymethacrylate | 0.64 | 0.64 | 0.64 | 0.64 |
| | PEG/PPG-17/6 Copolymer | 2.00 | 2.00 | 2.00 | 2.00 |
| | Acrylates/C10-30 Alkyl Acrylate Crosspolymer | 0.08 | 0.08 | 0.08 | 0.08 |
| | Tromethamine | 0.05 | 0.05 | 0.05 | 0.05 |
| Water-solubilizing part | Ethanol 95% | 4.00 | 4.00 | 4.00 | 4.00 |
| | PEG-60 Hydrogenated Castor Oil | 0.30 | 0.30 | 0.30 | 0.30 |
| | Phenoxyethanol | 0.30 | 0.30 | 0.30 | 0.30 |
| | Ethylhexylglycerin | 0.05 | 0.05 | 0.05 | 0.05 |
| | Fragnance | 0.10 | 0.10 | 0.10 | 0.10 |
| | Total sum | 100 | 100 | 100 | 100 |

TABLE 1

| Component | Content (wt %) | | | | | | | | | | |
|---|---|---|---|---|---|---|---|---|---|---|---|
| | Example 1 | Example 2 | Example 3 | Example 4 | Comparative Example 1 | Comparative Example 2 | Comparative Example 3 | Comparative Example 4 | Comparative Example 5 | Comparative Example 6 | Comparative Example 7 |
| 1,3-Propanediol | 94 | | | 90 | | | 74 | | | 60 | |
| Butylene Glycol | | 94 | | | | | | 74 | | | |
| Propylene Glycol | | | 94 | | | | | | 74 | | |
| D.I.Water | | | | | 94 | | | | | | |
| Glycerin | | | | 4 | | | | | | 34 | |
| Ethanol | | | | | | 94 | 20 | 20 | 20 | | 94 |
| Water-soluble amentoflavone-oligomer complex | 6 | 6 | 6 | 6 | 6 | 6 | 6 | 6 | 6 | 6 | 6 |
| Total sum | 100 | 100 | 100 | 100 | 100 | 100 | 100 | 100 | 100 | 100 | 100 |

<Production Example 2> Production of First Agent

In accordance with the composition of Table 2 below, the components corresponding to the water-soluble parts were dissolved and dispersed in distilled water using a mixer, and the components corresponding to the water-solubilizing parts were separately dissolved using a mixer, and the dissolved water-solubilizing part components were added to and mixed with the dissolved and dispersed water-soluble part components to prepare Examples 5 to 7 and Comparative Example 8. The unit of content in Table 2 below is the <Test Example 1> 4-Week Accelerated Stability Evaluation Test of Second Agent In order to compare and evaluate the 4-week accelerated stability of Examples 1 to 4 and Comparative Examples 1 to 7, samples were stored in an incubator (Jisico Co. Ltd.) at −15° C., 5° C., room temperature, 30° C., 45° C. and 60° C., and restored to room temperature weekly, and then stored, thereby confirming the forth week accelerated stability. The test results are shown in Table 3 below.

TABLE 3

|  | Example 1 | Example 2 | Example 3 | Example 4 | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|---|---|
| 4th week accelerated stability | ** | * | * |  |  | * |  |  |  |  | * | stability:
**** very excellent,
*** excellent,
** ordinary,
* bad

As shown in Table 3, in the case of Examples 1 to 4 in which amentoflavone-oligomer complex was stabilized by using 1,3-propanediol, butylene glycol, propylene glycol, or both 1,3-propanediol and a small amount of glycerin, it was confirmed that the fourth week accelerated stability was far superior as compared with Comparative Examples 1 to 7 using only purified water, glycerin or ethanol, or using 1,3-propanediol, butylene glycol, or propylene glycol together with ethanol, or using 1,3-propanediol and a large amount of glycerin together, in addition to the water-soluble amentoflavone-oligomer complex, and thus, the stability of amentoflavone was greatly improved in the second agent. In particular, when comparing Example 4 and Comparative Example 1, it was confirmed that since the amentoflavone-oligomer complex was water-solubilized, it was stable and the high-temperature precipitation was delayed even if the polarity of the solvent was adjusted by containing a small amount (20% or less) of glycerin in addition to the polyhydric alcohol.

<Test Example 2> Evaluation Test of Titer Stability of Second Agent

In order to evaluate the titer stability at 25° C. and 40° C. of Examples 1 to 4 and Comparative Examples 1 to 7, respectively, a high-performance liquid chromatography (HPLC) was used. The specification of the measuring device, measurement conditions and measurement results are shown in Table 4 below.

As shown in Table 4, in the case of Examples 1 to 4 in which the water-soluble amentoflavone-oligomer complex was stabilized by using 1,3-propanediol, butylene glycol, propylene glycol, or both 1,3-propanediol and a small amount of glycerin, it was confirmed that the titer stability was far superior at both 25° C. and 40° C. as compared with Comparative Examples 1 to 7 using only purified water, glycerin or ethanol, or using 1,3-propanediol, butylene glycol, or propylene glycol together with ethanol, or using 1,3-propanediol and a large amount of glycerin together, in addition to the water-soluble amentoflavone-oligomer complex, and thus, the stability of amentoflavone was greatly improved in the second agent.

<Test Example 3> Accelerated Stability Evaluation Test after Mixing of First Agent and Second Agent In order to evaluate the respective fourth week and eighth week accelerated stabilities after mixing Examples 5 to 7 and Comparative Example 8 with Example 1 at a mixing ratio of 5:1 on a weight basis, respectively, the accelerated stabilities were confirmed by the same method as in Test Example 1. The results of the fourth week accelerated stability evaluation test are shown in Table 5, and the results of the eighth week accelerated stability evaluation test are shown in FIG. 1.

TABLE 4

|  |  | Example 1 | Example 2 | Example 3 | Example 4 | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|---|---|---|
| Initial value |  | 0.4833 | 0.5100 | 0.5090 | 0.4893 | 0.5080 | 0.5110 | 0.4861 | 0.4845 | 0.4910 | 0.5070 | 0.4905 |
| Titer relative to initial value (%, elapsed for 4 weeks) | 25° C. | 103.2 | 92.4 | 103.2 | 100.2 | 88.5 | 65.0 | 87.4 | 77.7 | 82.1 | 85.0 | 60.0 |
|  | 40° C. | 99.3 | 87.5 | 99.3 | 99.9 | 75.8 | 45.6 | 83.6 | 73.6 | 83.7 | 84.7 | 58.0 |
| Specification of the measuring device and measurement conditions |  | Column: Mightysil RP-C18 (4.6 × 150 mm, 5 um) Elution solution: 10 mM KH$_2$PO$_4$:MeOH = 30:70 Extraction solvent: MeOH Detector: 340 nm Injection volume: 10 uL Staying time: 3.29 min Flow rate: 1.0 mL/min |||||||||||

TABLE 5

|  | Example 5 + Example 1 | Example 6 + Example 1 | Example 7 + Example 1 | Comparative Example 8 + Example 1 |
|---|---|---|---|---|
| 4$^{th}$ week accelerated stability after mixing | *** | *** | *** | ** |

Stability:
**** very excellent,
*** excellent,
** ordinary,
* bad

As shown in Table 5, in the case where Examples 5 to 7 containing at least one or more of niacinamide and D-panthenol as hydrotrope were mixed with Example 1, it was confirmed that the fourth week accelerated stability after mixing was excellent as compared with the case where Comparative Example 8 containing no hydrotrope was mixed with Example 1, and thus, amentoflavone was markedly stabilized even after mixing the first agent and the second agent.

In addition, as shown in FIG. 1, in the case where Examples 5 to 7 containing at least one or more of niacinamide and D-panthenol as hydrotrope were mixed with Example 1, it was confirmed that precipitation was delayed and thus a clear formulation was maintained, unlike the case where Example 1 was mixed with Comparative Example 8 containing no hydrotrope.

<Test Example 4> Titer Stability Evaluation Test after Mixing of First Agent and Second Agent In order to evaluate the respective titer stabilities after mixing Examples 5 to 7 and Comparative Example 8 with Example 1 at a mixing ratio of 5:1 on a weight basis, respectively, the titer stabilities were evaluated using HPLC with the same specifications and measurement conditions as in Test Example 2 above. The test results are shown in Table 6 below.

TABLE 6

|  | Example 5 + Example 1 | Example 6 + Example 1 | Example 7 + Example 1 | Example 8 + Example 1 |
|---|---|---|---|---|
| Amentoflavone content immediately after mixing (wt %) | 0.0839 | 0.0840 | 0.0841 | 0.0838 |
| Amentoflavone content after 1 week of mixing (wt %) | 0.0831 | 0.0833 | 0.0835 | 0.0701 |
| Titer (%) | 99.05 | 99.17 | 99.29 | 83.65 |

As shown in Table 6, in the case where Examples 5 to 7 containing hydrotrope according to the present invention are mixed with Example 1, it was confirmed that the titer stability was maintained at 99% or more as compared with the case where Comparative Example 8 containing no hydrotrope was mixed with Example 1, and thus, amentoflavone was greatly stabilized even after mixing the first agent and the second agent.

The invention claimed is:
1. A cosmetic product comprising a transparent or semi-transparent cosmetic composition having enhanced amentoflavone stability,
said cosmetic product comprising:
a first agent containing hydrotrope;
a second agent consisting of a water-soluble amentoflavone-oligomer complex, a polyhydric alcohol for stabilizing the amentoflavone, and optionally distilled water or glycerin; and
a two-liquid type container storing the first agent and the second agent, respectively, resulting in a mixture of the first agent and the second agent before use,
wherein the water-soluble amentoflavone-oligomer complex encapsulates the amentoflavone in a cavity structure of an oligomer structure formed from a hydrophilic natural polymer, and
wherein the water-soluble amentoflavone-oligomer complex is contained in an amount of 0.2 to 30% by weight based on the total weight of the second agent.
2. The cosmetic product according to claim 1, wherein the hydrotrope is one or more selected from the group consisting of niacinamide, caffeine, sodium pyrrolidone carbonic acid, sodium salicylate, urea, hydroxyethyl urea, and D-panthenol.
3. The cosmetic product according to claim 1, wherein the amentoflavone is in a form of a *Selaginella tamariscina* extract.
4. The cosmetic product according to claim 1, wherein the amentoflavone is encapsulated in the cavity structure in an amount of 7.6 to 9.2% by weight relative to the total weight of the water-soluble amentoflavone-oligomer complex.
5. The cosmetic product according to claim 1, wherein the water-soluble amentoflavone-oligomer complex is contained in an amount of 0.1 to 5% by weight based on the total weight of the transparent or semitransparent cosmetic composition.
6. The cosmetic product according to claim 1, wherein the polyhydric alcohol is a dihydric or trihydric alcohol having 3 to 6 carbon atoms.
7. The cosmetic product according to claim 1, wherein the polyhydric alcohol is at least one of propanediol and butanediol.
8. The cosmetic product according to claim 1, wherein the amentoflavone is contained in an amount of 0.0152 to 2.76% by weight based on the total weight of the second agent.
9. The cosmetic product according to claim 1, wherein the amentoflavone is contained in an amount of 0.0076 to 0.46% by weight based on the total weight of the transparent or semitransparent cosmetic composition.
10. The cosmetic product according to claim 1, wherein a mixing ratio of the first agent and the second agent is 1 to 6:1 on a weight basis.
11. The cosmetic product according to claim 1, wherein the second agent comprises distilled water or glycerin.
12. The cosmetic product according to claim 11, wherein the distilled water or glycerin is contained in an amount of greater than 0% by weight or less to 30% by weight based on the total weight of the second agent.

* * * * *